US00PP11580P

United States Patent [19]

Kent

[11] Patent Number: Plant 11,580

[45] Date of Patent: Oct. 17, 2000

[54] BROMELIAD PLANT NAMED 'GUZ 203'

[75] Inventor: Jeffrey C. Kent, Vista, Calif.

[73] Assignee: Kent's Bromeliad Nursery, Inc., Vista, Calif.

[21] Appl. No.: 09/114,410

[22] Filed: Jul. 13, 1998

[51] Int. Cl.[7] ..... A01H 5/00

[52] U.S. Cl. ..... Plt./371

[58] Field of Search ..... Plt./371

[56] References Cited

U.S. PATENT DOCUMENTS

P.P. 8,715 5/1994 Hill, Jr. ..... Plt./371

*Primary Examiner*—Howard J. Locker

*Assistant Examiner*—Wendy Anne Baker

*Attorney, Agent, or Firm*—James A. Lucas; Driggs, Lucas, Brubaker & Hogg Co., L.P.A.

[57] ABSTRACT

A hybrid Guzmania plant is compact in size, having a height including inflorescence of fourteen to sixteen inches and a spread of about twelve to thirteen inches. It has broad and closely-set leaves. The leaves are medium-dark green in color and contrast sharply with the vivid red color of the bracts.

1 Drawing Sheet

BACKGROUND OF THE DISCLOSURE

This application relates to a newly developed interspecific hybrid Guzmania plant resulting from a planned breeding program which I conducted on an ongoing basis. The objects of the breeding program include the crossing of selected parent plants from the numerous, compatible species within the genus, to obtain plants with novel and attractive phenotypes, coloration, and flowering forms. Other important selection factors may include ultimate plant size and shape, disease, resistance, tolerance to different soil and growing conditions and vigor.

Included objects of my program are to produce plants which will be attractive to the consumer; which will develop reasonably rapidly under controlled conditions; and, retain for a long term, highly attractive and bright inforescence; i.e., bract coloration, after being induced into the flowering stage. It is a specific object to provide a low maintenance plant which will be a long term decorative appointment whose bracts offer an exotic color splash in the home of a buyer even though its flowers are not prominent. Finally, it is an object to develop plants which may be easily and efficiently multiplied by state-of-the art tissue culture methods while continuing the distinctive characteristics of the plants through progressive clonal generations.

The plant of this disclosure was a selection from the progeny resulting from the cross of *Guzmania kraenzliniana,* var. kraenzliniana (seed parent) and *G. wittmackii* 'Tomato' (pollen parent). With the recognition that this seedling from the cross satisfied the objects of the breeding program, it was isolated and set aside for further observation and testing. The resulting selection has been assigned the designation 'GUZ 203' for purposes of identification. This plant has been reproduced by tissue culture at Evergem Belgium, and elsewhere, and the clonal specimens resulting have been determined to be identical to the original selection in all distinguishing characteristics. The superior attributes of this plant will be revealed in the botanical description to follow:

SUMMARY OF THE INVENTION

The attributes of the plant 'GUZ 203', which distinguish it from other plants of the Guzmania family, are summarized as follows:

It is smaller than other hybrids having an overall height including inflorescence of about 14 to 16 inches, and a spread of about 12 to 13 inches when finished to a stage of full bloom. It can be grown in 4" pots rather than a 6" pot in which most other Guzmania hybrids are grown. About one year is required to grow from a ½" high tissue cultured plant to market. Unlike most other Guzmania hybrids, which have a basal rosette of leaves from which a spike rises topped by a smaller rosette of colorful bracts and flowers, 'GUZ 203' is a more open rosette with fewer leaves, arranged more nearly horizontal. The leaves are small and reach lengths of about 8 to 9 inches and a width of about 1¼ inches. They are closely set, contributing to a compact plant. They are acuminate, tapering to abruptly pointed tips which are recurved and somewhat twisted. The leaves are smooth and medium dark green in color, obverse and reverse, stained red on reverse and light red in obverse, and blending into a strong reddish brown at the base.

The bracts are more distinctly and vividly colored than those of other hybrids and are in harmony with the darker leaves. The scape bracts are generally red in color on both the obverse and reverse blending into a reddish brown at the bract bases. The floral bracts are translucent red in color.

The attractive bright red bract color is rich and more vivid than the color of other hybrids and is retained indoors for more than two months.

BRIEF DESCRIPTION OF THE VIEW OF THE DRAWING

The single color photograph of the drawing depicts a mature specimen of the plant in top perspective angle in mid to late flowering stage. Illustrated are the mature leaves and the spike with small flowers hidden or nearly hidden in the cup formed by the floral bracts. The relative sizes of the lower, splayed intermediate and terminal bracts can be seen by the angle of the illustration. The colors depicted are as close to the actual coloration of the plant as is possible to attain in a photographic illustration of this quality, however due to factors such as light reflectance, minor differences in coloration do appear.

The color definitions in the specification to follow have been taken from The Royal Horticultural Society Colour Chart. While the colors depicted are believed to be of a high level of color fidelity, the coloration of this plant should be understood to be approximate, and somewhat variable as a function of cultural conditions and horticultural practices. For example, the bract color might slightly fade if the plant is cultured in bright light; the leaf color can be varied by the composition and concentration of fertilizer applied to specimens of the plant.

BOTANICAL DESCRIPTION OF THE PLANT

Parentage: Seedling.

*Seed parent.*—*Guzmania kraenzliniana,* var. kraenzkiniano.

*Pollen parent.*—*Guzmania wittmackii* 'Tomato'.

Propagation: Asexual reproduction by tissue culture.

Classification:

*Monocot, Perennial.*—Small, vigorous to anthesis relative to other bromeliad varieties, upright, spreading dense, vase formed, and tender.

*Overall height from soil surface.*—14"–16" including inflorescence.

*Overall width.*—12"–13".

Leaves:

*Length.*—8¼".

*Width.* 1¼"

The mature plant has between about 12 and 18 leaves. Small, linear, acuminate, acutely pointed medium thickness, medium to dark green and smooth. 135-A in color. (Obverse and reverse) Stained 181A on reverse, lightly on obverse, blending into lines of 45-B color at base.

*Margin.*—Leaf tips recurved and somewhat twisted.

Flower buds: Hardiness at temperatures below 32° F. Tender, medium in size, medium length (1"×3/16"), pointed and appressed.

*Scape bracts.*—6¼"×1½", narrow deltoid, clasping decreasing to 4"×1." 45C in color, obverse and reverse blending into 46A at bract bases on reverse, infrequently on obverse.

*Floral bracts.*—1⅛"×3/16", linear acute, keeled longitudinally throughout. Translucent 53C in color, irregularly lined and stained 45C. The plant has between about 10 and 16 bracts (floral and scape):

Inforescence a branched spike.

Flowers: Petals free to base, recurved and twisted at anthesis. Corolla cylindrical and acute. 3 sepals ⅞×3/16", stained 56-C in color. 3 petals 1⅛"×¼", 73-D in color.

Fruit: A three-celled capsule, with pappus.

Disease resistance: No unusual susceptibility to diseases of Guzmania has been noted.

I claim:

1. A new and distinct variety of Guzmania plant substantially as shown and described, characterized by a compact size, broad and closely-set leaves, and a sharp contrast between the bract color and the medium-dark green leaf coloration, the bract retaining a rich, vivid red color indoors for eight weeks.

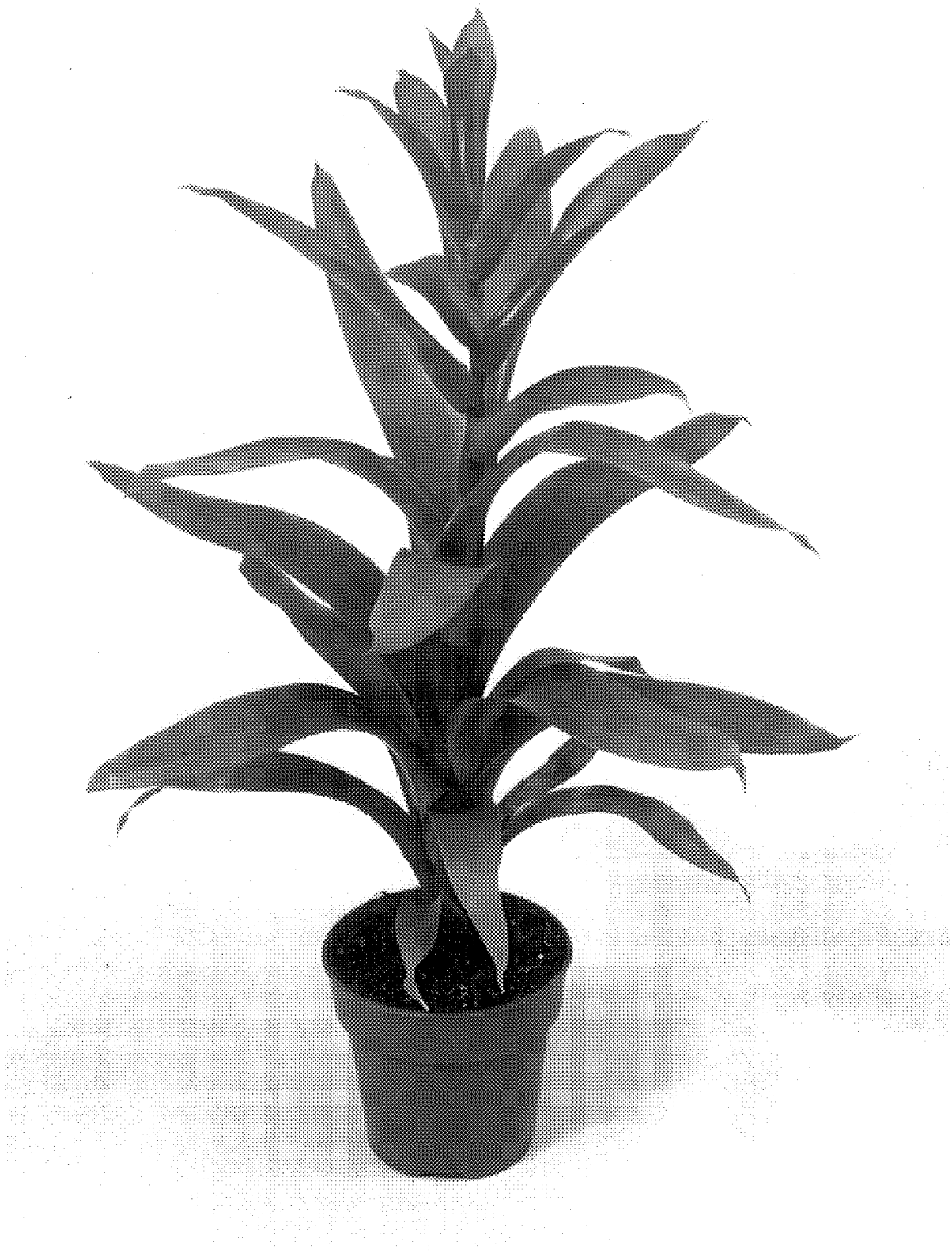

* * * * *